(12) United States Patent
Dev et al.

(10) Patent No.: US 12,053,447 B2
(45) Date of Patent: Aug. 6, 2024

(54) ORAL SOLUTION AND POWDER TO LIQUID COMPOSITIONS OF BALSALAZIDE

(71) Applicant: NuBioPharma, LLC, Stanford, NC (US)

(72) Inventors: Inderjit Kumar Dev, Durham, NC (US); Ajay Kumar Ajmani, Pittsboro, NC (US); Ronald Lee Morris, Jr., Mooresville, NC (US)

(73) Assignee: NuBioPharma, LLC, Stanford, NC (US)

( * ) Notice: Subject to any disclaimer, the term of this patent is extended or adjusted under 35 U.S.C. 154(b) by 155 days.

(21) Appl. No.: 16/452,151

(22) Filed: Jun. 25, 2019

(65) Prior Publication Data
US 2020/0405673 A1 Dec. 31, 2020

(51) Int. Cl.
| | |
|---|---|
| A61K 31/197 | (2006.01) |
| A61K 9/00 | (2006.01) |
| A61K 35/741 | (2015.01) |
| A61K 35/742 | (2015.01) |
| A61K 35/745 | (2015.01) |
| A61K 35/747 | (2015.01) |
| A61K 47/02 | (2006.01) |
| A61K 47/12 | (2006.01) |
| A61K 47/18 | (2017.01) |
| A61K 47/22 | (2006.01) |
| A61K 47/26 | (2006.01) |

(52) U.S. Cl.
CPC .......... *A61K 31/197* (2013.01); *A61K 9/0053* (2013.01); *A61K 9/009* (2013.01); *A61K 35/741* (2013.01); *A61K 35/742* (2013.01); *A61K 35/745* (2013.01); *A61K 35/747* (2013.01); *A61K 47/02* (2013.01); *A61K 47/12* (2013.01); *A61K 47/186* (2013.01); *A61K 47/22* (2013.01); *A61K 47/26* (2013.01)

(58) Field of Classification Search
CPC .... A23V 2250/264; A61K 9/00; A61K 47/26; A61K 9/0053; A61K 47/22; A23L 27/00; A23L 27/12
USPC ................................. 424/400, 548
See application file for complete search history.

(56) References Cited

U.S. PATENT DOCUMENTS

| | | |
|---|---|---|
| 5,154,926 A | 10/1992 | Kawasaki et al. |
| 5,458,879 A | 10/1995 | Singh et al. |
| 5,616,621 A | 4/1997 | Popli et al. |
| 5,763,449 A | 6/1998 | Anaebonam et al. |
| 5,962,461 A | 10/1999 | Anaebonam et al. |
| 6,197,341 B1 | 3/2001 | Friess et al. |
| 6,326,364 B1 | 12/2001 | Lin et al. |
| 6,391,886 B1 | 5/2002 | Lee |
| 6,649,186 B1 * | 11/2003 | Robinson ............. A61K 9/0034 424/489 |
| 6,806,256 B2 | 10/2004 | Ulrich et al. |
| 6,911,214 B2 | 6/2005 | Alani et al. |
| 7,101,572 B2 | 9/2006 | Santos et al. |
| 7,758,877 B2 | 7/2010 | Asotra et al. |
| 7,928,092 B2 | 4/2011 | Devane et al. |
| 7,973,070 B2 | 7/2011 | Mori et al. |
| 8,362,083 B2 | 1/2013 | Djordjevic et al. |
| 8,455,662 B2 | 6/2013 | Hashash et al. |
| 8,591,938 B2 | 11/2013 | Tarallo |
| 8,703,156 B2 | 4/2014 | Spino et al. |
| 8,758,779 B2 | 6/2014 | Mate et al. |
| 9,040,089 B2 | 5/2015 | Walzade et al. |
| 9,095,577 B2 | 8/2015 | Myers et al. |
| 9,616,121 B2 | 4/2017 | Agrawal |
| 9,757,394 B2 | 9/2017 | Pipho et al. |
| 2003/0118654 A1 | 6/2003 | Santos et al. |
| 2006/0024335 A1 * | 2/2006 | Roger ................. A61K 9/0095 424/400 |
| 2006/0024370 A1 | 2/2006 | Nguyen et al. |
| 2006/0141031 A1 * | 6/2006 | Nelson ................. A61K 9/2077 424/464 |
| 2009/0252788 A1 * | 10/2009 | Lockhart ............. A61K 31/655 424/455 |
| 2009/0274662 A1 * | 11/2009 | Magowan ............. A61K 33/24 424/93.4 |

(Continued)

OTHER PUBLICATIONS

Pubchem: acesulfame, 2 pages.*
Pubchem: ammonium glycyrrhizinate, 2 pages.*
Mennella et al., Clinical Therapeutics, 30, 2008, 2120-2132.*
Pubchem: acesulfame, 2 pages, 2023, https://pubchem.ncbi.nlm.nih.gov/compound/Acesulfame (previously cited May 15, 2023; date + URL added for clarity of record).*
Pubchem: ammonium glycyrrhizinate, 2 pages, 2023, https://pubchem.ncbi.nlm.nih.gov/compound/Ammonium-glycyrrhizate ( previously cited May 15, 2023; date + URL added for clarity of record).*

(Continued)

*Primary Examiner* — Kyle A Purdy
(74) *Attorney, Agent, or Firm* — Joshua S. Schoonover

(57) ABSTRACT

A pharmaceutical composition for preparation of an orally administered liquid solution containing a therapeutically sufficient dose of dissolved balsalazide. The composition further comprises three artificial sweeteners comprising sucralose, acesulfame potassium and ammonium glycyrrhizinate that unexpectedly mitigate the bitter attributes of the orally administered liquid balsalazide solution that would otherwise render the solution unpalatable. More particularly, the present disclosure relates to a composition of the three artificial sweeteners and a therapeutically sufficient dose of balsalazide for the treatment of bowel disorders such as ulcerative colitis. Unit dose sachets of balsalazide disodium 750 mg and 2,250 mg of powder to oral solution are also disclosed. The disclosure further provides a kit including a dissolvable solid phase composition of the three artificial sweeteners and dissolvable solid phase therapeutically sufficient dose of balsalazide and further comprising a therapeutic dose of a probiotic (*bacillus*) to enhance the azoreduction of the balsalazide in the colon.

1 Claim, 5 Drawing Sheets

(56) References Cited

U.S. PATENT DOCUMENTS

| | | | |
|---|---|---|---|
| 2010/0010101 A1* | 1/2010 | Cherukuri | A61K 9/2095 514/784 |
| 2011/0136851 A1 | 6/2011 | Jaeger et al. | |
| 2015/0216806 A1 | 8/2015 | Borody | |
| 2015/0297642 A1 | 10/2015 | Borody | |
| 2016/0143310 A1 | 5/2016 | Santos et al. | |
| 2017/0312322 A1 | 11/2017 | Rohwer et al. | |
| 2018/0296495 A1* | 10/2018 | Lee | A61K 31/164 |

OTHER PUBLICATIONS

Chan-Ju Wang. Role of tyrosine 131 in the active site of paAzoR1, an azoreductase with specificity for the inflammatory bowel disease prodrug balsalazide. Structural Biology and Crystallization Communications. 2010.

Fatemeh Rafii. Azoreductase Activity of Anaerobic Bacteria Isolated from Human Intestinal Microflora. Applied and Environmental Microbiology. Jul. 1990.

Jeffrey S. Hyams, Sorbitol Intolerance: An Unappreciated Cause of Functional Gastrointestinal Complaints. Gastroenterology. 1983.

Mäkinen. Gastrointestinal Disturbances Associated with the Consumption of Sugar Alcohols with Special Consideration of Xylitol: Scientific Review and Instructions for Dentists and Other Health-Care Professionals. International Journal of Dentistry vol. 2016.

Michelle A. McConnell. Lactobacilli and Azoreductase Activity in the Murine Cecum. Applied and Environmental Microbiology. Dec. 1991.

Toshihiko Ooi. Comparative Enzymatic Analysis of Azoreductases from Bacillus. Biosci. Biotechnol. Biochem., 2009.

* cited by examiner

ORAL SOLUTION AND POWDER TO LIQUID COMPOSITIONS OF BALSALAZIDE

BACKGROUND

The following relates generally to compositions containing balsalazide, and more specifically to a composition comprising a combination of sweeteners for masking the bitterness of balsalazide.

Balsalazide disodium is indicated for the treatment of inflammatory gastrointestinal diseases, for example: mild to moderately active ulcerative colitis (UC), radiation proctosigmoiditis, diverticulitis, irritable bowel syndrome (IBS) and colon cancer. Balsalazide is a colon-specific, non-steroidal, anti-inflammatory amino salicylate derivative. Balsalazide is a pro-drug containing the active agent 5-aminosalicylic acid (5-ASA), linked to a 4-amino benzoyl-3-alanine ("4-ABA") moiety by a diazo bond and is delivered intact past the small intestine to the large intestine, the active site of UC and other diseases. An azoreductase produced by bacteria in the colon cleaves the diazo link to release the active agent 5-aminosalicylic acid (ASA). Other drugs suitable for using the pro-drug approach include 5-aminosalicylic acid (ASA) in the form of sulfasalazine, olsalazine and ipsalazine, and for its positional isomer 4-ASA—a well-established antitubercular drug that is twice as potent as 5-ASA against IBD, and more specifically, ulcerative colitis.

Balsalazide may be provided as solid dosage forms of capsules (750 mg) and tablets (1100 mg). Several large capsules or tablets at a time are needed for the treatment. The usual dose is 2250 mg (three 750 mg capsules) taken three times daily for 8 to 12 weeks or three 1.1 g tablets two times a day for up to 8 weeks. The daily dose is either three 750 mg balsalazide capsules 3 times a day (6.75 g/day), or three 1100 mg balsalazide tablets 2 times a day (6.6 g/day). Due to this high pill burden a majority of patients do not adhere to balsalazide treatment and non-adherence rates are very high (69%). Adherence to balsalazide therapy is needed to eradicate active symptoms, lower risk of colorectal cancer, prevent relapse and reduce risks of hospitalization and surgery. Adherent patients have less inflammation, less need for steroid use, and a lower risk of future colectomy with mucosal healing.

Non-compliance to balsalazide therapy is further exacerbated in children, older people, and many sick patients who often have trouble swallowing the large tablets or capsules. A liquid formulation of a drug that is easily swallowed is the most desirable formulation for use in these situations. However, a liquid solution of balsalazide is disagreeably bitter, acrid, and so pungent as to render it unpalatable. Moreover, the addition of high levels of sucrose, or corn syrup in an attempt to overwhelm the bitterness of a liquid therapeutic dose of balsalazide is ineffective as it results in precipitation of the balsalazide.

There is a need to provide a palatable liquid composition for the oral delivery of balsalazide, as well as other diazo pro-drugs for the treatment of gastrointestinal diseases, in therapeutically sufficient dosages so as to avoid the swallowing of large capsules which can be difficult or impossible for the elderly, and small children. Such a liquid composition must mitigate the bitterness of the pro-drug, and in the particular case of treating a gastrointestinal disorder it must mitigate the bitterness without the use of polyols and additional sodium salts.

SUMMARY

Compositions, methods, and kits are provided for the preparation and oral delivery of a liquid chemical composition for treatment of chronic inflammatory gastrointestinal diseases. More particularly, the present disclosure relates to a composition for the preparation and delivery of a palatable liquid oral solution of balsalazide in therapeutically sufficient dosages.

As used herein "percent w/v" refers to the percent weight of the total liquid composition. As used herein "percent w/w" refers to the percent weight of the total powder composition.

References throughout this document to "one embodiment", "certain embodiments" and "an embodiment" or similar terms means that a particular feature, structure, or characteristic described in connection with the embodiment is included in at least one embodiment of the present disclosure. Thus, the appearances of such phrases in various places throughout this specification are not necessarily all referring to the same embodiment. Furthermore, the particular features, structures, or characteristics may be combined in any suitable manner in one or more embodiments without limitation.

The expression "free of additional sodium salts" is intended to define a formulation without a determinable amount of additional sodium salts, while the term "sodium salts" is intended to include all the salts containing sodium such as sodium chloride, sodium citrate, sodium bicarbonate, etc.

As used herein a unit dose powder is an aliquot containing a single therapeutic dose of a balsalazide disodium formulation.

The pharmaceutical formulation of the sachet can be formulated as a powder, granules or pellets. The powder, granules or pellets or their mixtures may be a ready to use sachet's formulation which can be consumed directly from the packet or subsequently after the addition of water.

The expression "polyol-free" is intended to define a formulation without a determinable amount of polyols or at least less than 0.01% w/w, while the term "polyols" is intended to include all the alcohols containing multiple hydroxyl groups. "Sugar alcohols" is a class of polyols that include erythritol, arabitol, xylitol, mannitol, sorbitol, isomalt, maltitol, and lactitol. Polyols also include monomeric polyols such as glycerol, pentaerythritol, propylene glycol and ethylene glycol, which often serve as the starting point for polymeric polyols. Polymeric polyols are usually polyethers or polyesters. Common polyether diols are polyethylene glycols, polypropylene glycol, and poly (tetramethylene ether) glycol.

"Therapeutically effective amount" of balsalazide refers to a dosage or an amount of balsalazide which is effective, upon single or multiple dose administration to a mammal, that is sufficient to reduce, alleviate, prevent or ameliorate the symptoms of gastrointestinal disease in a mammal or to achieve a desired biological outcome.

The term, "gastrointestinal disease or disorder" refers to and includes, for example, ulcerative colitis, Crohn's disease, irritable bowel syndrome, colon cancer, diverticulitis, and proctitis (e.g., radiation induced proctitis).

A chemical composition including a combination of sweeteners for masking the bitterness of balsalazide is described. The chemical composition may include a prodrug therapeutic agent selected from at least one of balsalazide, balsalazide disodium, sulfasalazine, olsalazine and ipsalazine, the positional balsalazide isomer 4-aminosalicylic acid, linked to 4-amino benzoyl-3-alanine and its disodium salt in the range from about 52% w/w to 99% w/w of the chemical composition, the therapeutic dose being sufficient to provide between 750 mg to 3,300 mg of the therapeutic agent, and a sweetener composition for mitigating the bitterness of the therapeutic agent comprising sucralose in the range of 0.30% w/w to 6.0% w/w of the chemical composition, acesulfame potassium in the range of 0.30% w/w to 6.0% w/w of the chemical composition, ammonium glycyrrhizinate in the range of 0.10% w/w to 10.44% w/w of the chemical composition, and less than 0.01% of a polyol.

A method for preparation for oral liquid delivery of a therapeutically sufficient dose of a chemical composition for the treatment of a gastrointestinal disease is described. The method may include providing a chemical composition comprising a pro-drug and sugar composition; mixing the chemical composition in a mixing drum to obtain the chemical composition in a homogeneous powder form; providing and mixing flow control and anti-caking excipients. The preparation may then be packaged in sachets or pressed into tablets. Alternately, the processing may further include mixing the chemical composition and excipients in a homogeneous powder form with a short chain alcohol to provide a moistened chemical composition; granulating the moistened chemical composition; and drying the granulated chemical composition. The chemical composition now comprising a prodrug therapeutic agent selected from at least one of balsalazide, balsalazide disodium, sulfasalazine, olsalazine and ipsalazine, the positional balsalazide isomer 4-aminosalicylic acid, linked to 4-amino benzoyl-3-alanine and its disodium salt in the range from about 52% w/w to 99% w/w of the chemical composition, the therapeutic dose being sufficient to provide between 750 mg to 3,300 mg of the therapeutic agent, and a sweetener composition for mitigating the bitterness of the therapeutic agent comprising sucralose in the range of 0.30% w/w to 6.0% w/w of the chemical composition, acesulfame potassium in the range of 0.30% w/w to 6.0% w/w of the chemical composition, ammonium glycyrrhizinate in the range of 0.10% w/w to 10.44% w/w of the chemical composition, and less than 0.01% of a polyol. Additionally, the chemical composition may include a pH buffer, and taste competitors. Further processing may include the addition and mixing of an effervescent composition to provide a rapidly dissolving effervescent chemical composition containing a therapeutic dose of the desired pro-drug.

A therapeutic kit for the treatment of gastrointestinal disease is described. The therapeutic kit may include a unit dose of a non-toxic, beneficial probiotic containing intestinal microflora comprising at least one of beneficial strains of *Bacteroides* sp., beneficial strains of *Butyrivibrio* sp., *Bacillus subtilis*, *Bifidobacterium bifidum*, *Bifidobacterium lactis*, *Bifidobacterium longum*, *Bifiobacterium breve*, *Lactobacillus sporogenes*, *Lactobacillus rhamnosus*, *Lactobacillus casei*, *Lactobacillus salivarius*, *Lactobacillus acidophilus*, *Lactobacillus brevis*, *Lactobacillus paracasei*, *Eubacterium hadrum* 1, *Eubacterium* hadrum 2, *Eubacterium* sp., *Clostridium nexile*, *Clostridium* sp., *Clostridium clostridioforme*, and other non-toxic bacterium known for catalyzing the activation of the prodrug; and a unit dose of a chemical composition disposed in a hermetically sealed sachet as powder, granules, or effervescent tablet. The chemical composition comprises a pharmaceutically sufficient dose of a prodrug therapeutic agent selected from at least one of balsalazide, balsalazide disodium, sulfasalazine, olsalazine and ipsalazine, the positional balsalazide isomer 4-aminosalicylic acid, linked to 4-amino benzoyl-3-alanine and its disodium salt in the range from about 52% w/w to 99% w/w of the chemical composition, the therapeutic dose being sufficient to provide between 750 mg to 3,300 mg of the therapeutic agent, and a sweetener composition for mitigating the bitterness of the therapeutic agent comprising sucralose in the range of 0.30% w/w to 6.0% w/w of the chemical composition, acesulfame potassium in the range of 0.30% w/w to 6.0% w/w of the chemical composition, ammonium glycyrrhizinate in the range of 0.10% w/w to 10.44% w/w of the chemical composition, and less than 0.01% of a polyo. Optionally, the chemical composition may further include a taste competitor, a buffering agent, and inert excipients to facilitate processing.

A sweetener composition for mitigating the bitterness of a chemical composition is described. The sweetener composition may comprise sucralose in the range of 0.30% w/w to 6.0% w/w of the chemical composition, acesulfame potassium in the range of 0.30% w/w to 6.0% w/w of the chemical composition, ammonium glycyrrhizinate in the range of 0.10% w/w to 10.44% w/w of the chemical composition, and less than 0.01% of a polyol.

In some examples of the chemical composition, method, therapeutic kit, and sweetener described above, the prodrug is balsalazide disodium and the sweetener composition is polyol-free.

Some examples of the chemical composition, method, therapeutic kit, and sweetener composition described above may further include a taste competitor selected from at least one of citric acid, potassium salts of citric acid, and calcium salts of citric acid; phosphoric acid, potassium salts of phosphoric acid, and monobasic calcium salts of phosphoric acid; potassium chlorides; a hydroxy acid, and potassium bicarbonate.

In one embodiment of the chemical composition, method, therapeutic kit, and sweetener composition described above may further include taste receptor competitors comprising potassium dibasic phosphate anhydrous in the range of 5.02% w/w to 11.44% w/w, a taste competitor comprising citric acid is in the range of 0.90% w/w to 2.04% w/w, and a flavor excipient in the range of 0.76% w/w to about 1.74% w/w of the chemical composition.

Some examples of the chemical composition and sweetener composition will include excipient ingredients. Excipient ingredients such as magnesium stearate may be added for its lubricating properties, prevent lumping of individual ingredients with each other, and for preventing ingredients from sticking to manufacturing equipment during the compression of chemical powders into solid tablets. It also helps to enhance the therapeutic effect of the active ingredient of various medications to promote drug absorption and solubility. Colloidal silicon dioxide may also be added as an anti-caking agent, adsorbent, disintegrant, or glidant to allow powder to flow freely when tablets are processed. Only a miniscule amount of these excipients is required to coat a powder blend of the chemical composition of this invention.

In some examples of the chemical composition, method, therapeutic kit, and sweetener composition described above, the chemical composition is packaged in a therapeutically sufficient dose into a sachet. In some examples of the chemical composition, method, therapeutic kit, and sweetener composition described above, the sachet is packaged with a plurality of sachets into a container to provide a quantity of sachets sufficient for a course of treatment.

In one embodiment of the chemical composition, method, therapeutic kit, and sweetener composition described above, the chemical composition is combined with an effervescent composition comprising anhydrous citric acid and potassium bicarbonate to provide an effervescent chemical composition for rapid aqueous dissolution. In some examples of the chemical composition, method, therapeutic kit, and sweetener composition described above, the effervescent composition is formed into tablets to provide a therapeutically sufficient unit dose of a pro-drug therapeutic agent when dissolved in a liquid.

In some examples of the chemical composition, method, therapeutic kit, and sweetener composition described above, the chemical composition is packaged with a probiotic in accordance with a prescribed course of treatment.

DETAILED DESCRIPTION

Figure 1:
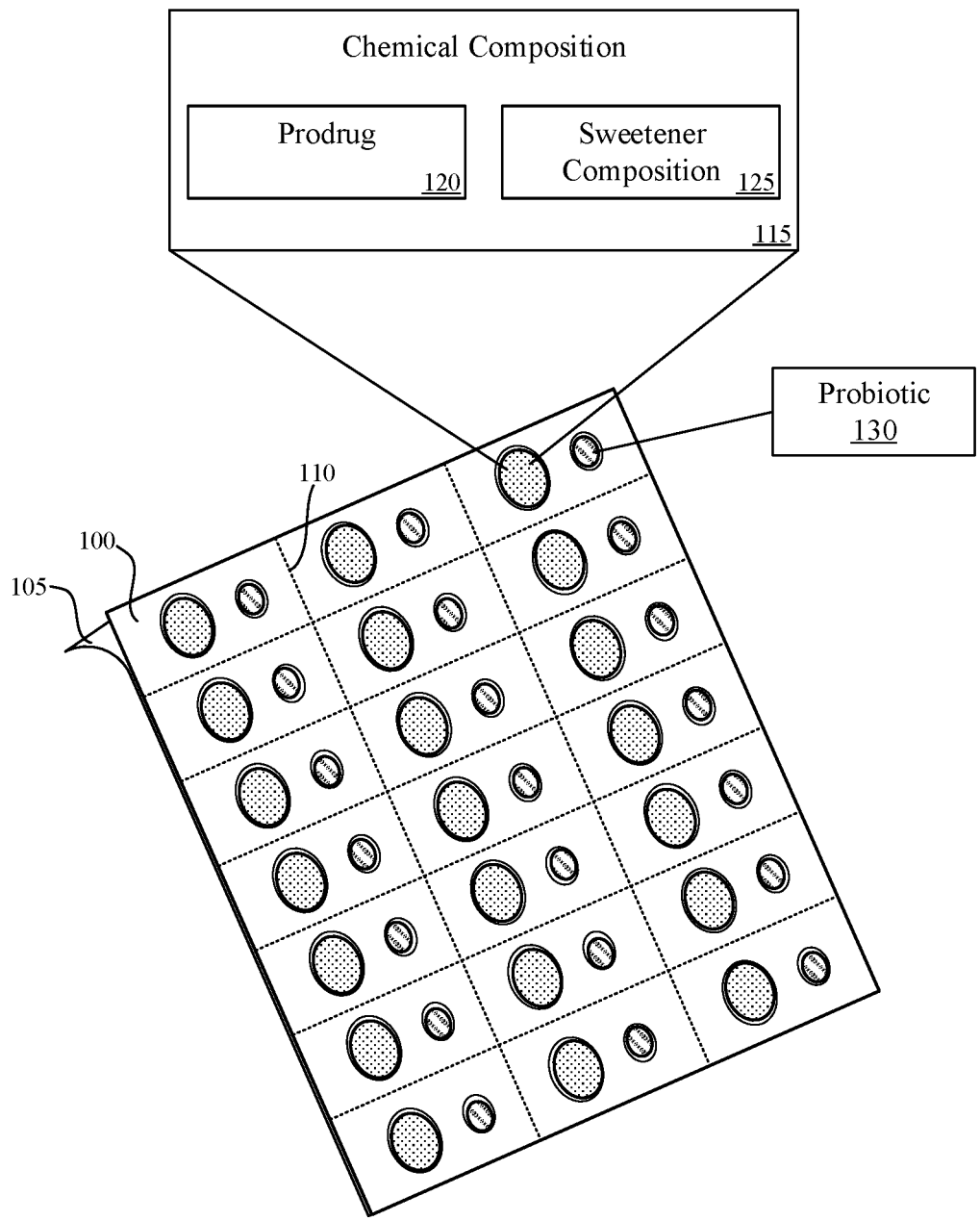
FIG. 1 shows an example of a blister pack with therapeutic dose and probiotic in accordance with aspects of the present disclosure.

The present disclosure relates to a therapeutic balsalazide composition for preparation of a palatable balsalazide oral solution providing an easy to swallow alternative to capsule and tablet dosing. In one embodiment a chemical composition includes a therapeutic dose of balsalazide or its pharmaceutically acceptable salts including balsalazide disodium, a sweetener composition of effective amounts of artificial sweeteners, and optionally, effective amounts of one or more taste receptor competitor agents that impart salty or sour taste, pH buffer agents and natural flavors. Since azoreductases in intestinal microflora are essential for activation of azo prodrugs in the treatment of inflammatory bowel disease and other gastrointestinal diseases, the kit of our disclosure may include at least one probiotic to repopulate the colon with intestinal microflora necessary for the azoreductase activation of the 5-ASA. Dissolution of this chemical composition in a liquid results in a palatable pharmaceutically sufficient liquid oral dose of balsalazide exhibiting a substantially reduced pungent and bitter taste than would otherwise be expected from a liquid oral composition containing balsalazide disodium.

Sweetener Composition and Taste Masking

A liquid solution of balsalazide is disagreeably bitter, acrid, and so pungent as to render it unpalatable. We have found that the addition of high levels of sucrose, or corn syrup in an attempt to overwhelm the bitterness of a liquid therapeutic dose of balsalazide is ineffective as it results in precipitation of the balsalazide. Using such large quantities of a natural sugar or corn syrup is not feasible since a very concentrated solution of balsalazide is needed to provide a dose of either 2.25 g to 3.3 g of drug 3 or 2 times per day, respectively. We have found that addition of these sugars to a concentrated solution of balsalazide makes it unstable and results in precipitation of the pro-drug. Other taste masking techniques include coating the bitter drug with a suitable polymer, spray drying with certain hydrophilic polymers, complex formation with ion exchange resin, inclusion complex formation with cyclodextrin, solid dispersion by co-precipitate method, microencapsulation technique, and prodrug approach etc. However, these techniques would add more mass to a liquid oral solution of balsalazide and make it unstable and are thus not feasible for the liquid oral delivery of a therapeutically sufficient dose of balsalazide.

Taste masking of a bitter drug using polyols (sugar alcohols) may include polyethylene glycol, propylene glycol, glycerol, sorbitol, xylitol, and D-mannitol. It should be noted, however, that since the liquid chemical composition is being used to treat inflammatory GI diseases, polyols (sugar alcohols) cannot be used as a taste masking agent. During inflammation associated with GI diseases, inflammation of the large intestine leads to bleeding sores or ulcers and diarrhea. Symptoms related to inflammation of the GI tract include abdominal cramps and pain, blood or pus in the stool, frequent and recurring diarrhea, an urgent need to evacuate the bowels, a sensation of incomplete evacuation, and constipation that can lead to bowel obstruction. Polyols can exacerbate these symptoms as they can cause GI disturbances and are frequently linked to irritable bowel syndrome (IBS) and abnormal flatulence. Intolerance to polyol and related compounds in patients with inflammatory GI diseases is therefore a major problem. It is desired, therefore, that when administering oral liquid pharmaceutical compositions to these patients that these compositions be free of polyols and related compounds.

In one embodiment, the above described balsalazide compositions are free from polyols (sugar alcohols) like polyethylene glycol, propylene glycol, glycerol, sorbitol, xylitol, and D-mannitol thus making it suitable for people suffering from GI inflammatory diseases who can therefore be treated with such embodiments of the disclosure.

In addition to the water and pungent or bitter-tasting balsalazide, a solution of the chemical composition of this disclosure also contains effective amounts of a taste masking combination of artificial sweeteners and effective amounts of one or more agents that impart salty or sour taste and natural flavors, which reduce or eliminate the disagreeable taste attributable to balsalazide, resulting in a more pleasant-tasting oral composition. The taste masking effective amount of an artificial sweetener is that amount whereby the taste of the bitter tasting pharmaceutically active agent balsalazide is masked and the liquid pharmaceutical composition is palatable.

Although aspartame, sucralose, acesulfame potassium and ammonium glycyrrhizinate are known taste-masking agents, we have found that none of these sweeteners alone or with other sweeteners and flavoring agents are sufficient to mask the bitter taste of balsalazide. Unexpectedly, the combination of three of these specific artificial sweeteners appear to surprisingly potentiate each other to provide the desired taste-masking effect.

In one embodiment the artificial sweetener composition consists of sucralose, acesulfame potassium and ammonium glycyrrhizinate. While aspartame may be used as an alternative component to acesulfame potassium, we have found that aspartame, while initially effective when combined with sucralose and ammonium glycyrrhizinate, became unstable in a liquid solution, thus prompting the use of the equally effective acesulfame potassium as the third artificial sweetener in this composition.

Sucralose (SPLENDA®) 1,6-dideoxy-b-D-fructofuranosyl-4-chloro-4-deoxy-α-D-galactopyranoside is an intensely sweet, trichlorinated carbohydrate, structurally similar to sucrose, approximately 600 times as sweet as sucrose, three times as sweet as both aspartame and acesulfame potassium, and twice as sweet as sodium saccharin. It is very much soluble in water and is stable over a wide range of pH and temperature.

Preferably, the taste masking effective amount of sucralose has a range of from about 0.05 to about 2.5 grams per 100 ml. More preferably, the taste masking effective amount of sucralose has a range of from about 0.10 to about 0.50 grams per 100 ml. More preferably, the taste masking effective amount of sucralose is about 0.20 gram per 100 ml.

Ammonium glycyrrhizinate is a triterpenoide glycoside (saponin) that consists of an aglycone of glycyrrhetic acid and a sugar moiety of two glucuronic acid units linked to each other and is extracted from Licorice Root. It is 50-100 times sweeter than sucrose and has a slow onset of sweetness followed by a lingering licorice-like aftertaste. It exhibits a sweet woody flavor, which limits its use as a pure sweetener. Ammonium glycyrrhizinate is used to enhance flavor and mask bitter flavors in food, beverages, nutraceuticals, pharmaceuticals, personal care products, cosmetics, and oral health products.

Preferably, the taste masking effective amount of ammonium glycyrrhizinate has a range of from about 0.02 to about 1.5 grams per 100 ml. More preferably, the taste masking effective amount of ammonium glycyrrhizinate has a range of from about 0.05 to about 1.0 grams per 100 ml. More preferably, the taste masking effective amount of ammonium glycyrrhizinate is about 0.50 gram per 100 ml.

Acesulfame potassium (Sunett® and Sweet One®) is 200 times sweeter than sucrose, as sweet as aspartame, about two-thirds as sweet as saccharin, and one-third as sweet as sucralose. Like saccharin, it has a slightly bitter aftertaste, especially at high concentrations.

Preferably, the taste masking effective amount of Acesulfame potassium has a range of from about 0.10 to about 3.0 grams per 100 ml. More preferably, the taste masking effective amount of Acesulfame potassium has a range of from about 0.10 to about 0.50 grams per 100 ml. More preferably, the taste masking effective amount of Acesulfame potassium is about 0.1 gram per 100 ml.

In one embodiment of the sweetener composition of this disclosure, effective amounts of the artificial sweeteners aspartame, sucralose, acesulfame potassium and ammonium glycyrrhizinate are combined to mask the pungent, bitter taste of balsalazide. We have found that a combination of effective amounts of three artificial sweeteners comprising sucralose, acesulfame potassium and ammonium glycyrrhizinate is unexpectedly effective at masking the pungent or bitter taste of a bitter drug, and in particular, balsalazide. The resulting effectiveness in mitigating the bitterness of a liquid balsalazide solution is surprising in that the combination of these three artificial sweeteners is the only one amongst many tested which yielded positive results.

In another embodiment, the chemical composition contains effective amounts of the sweetener composition of the combination of artificial sweeteners of the present disclosure, as well as effective amounts of one or more agents that impart salty or sour taste and natural flavors, which further reduce or eliminate the disagreeable taste attributable to balsalazide, resulting in an even more pleasant-tasting oral composition.

Taste Receptor Competitors

The use of various sodium salts like sodium chloride, sodium citrate and sodium bicarbonate may be used to reduce the bitter taste of drugs. For example, the use of sodium bicarbonate in combination with other ingredients have been used to reduce the bitter taste of active substances such as ciprofloxacin, paracetamol, erythromycin. Sodium chloride and sodium citrate have been used as taste receptor competitors or taste modifiers to mask the unpleasant and disagreeable taste of drugs. However, the use of these taste receptor competitors and taste modifiers is not desirable in view of the large amount of sodium already present in a therapeutic dose of balsalazide. A liquid formulation of balsalazide should contain little or no additional sodium salt since when administered at recommended doses (6.6 g/day), balsalazide disodium already includes about 756 mg of sodium per day. Any additional sodium would create problems for patients on sodium-restricted diet such as high blood pressure, heart disease and stroke, and also make the patient prone to osteoporosis, or thinning of the bones, since high salt tends to leach calcium out of your bones.

According to another embodiment, the above described balsalazide compositions are free from any additional sodium salts. This further advantage makes it suitable for patients on sodium-restricted diet who can therefore be treated with such embodiments of the disclosure.

One or more agents that compete with bitter-tasting balsalazide for taste receptors may be included in the chemical compositions of this disclosure. Taste receptor competitors generally include those substances which ordinarily impart a salt or sour taste. Examples of suitable taste-receptor competitors include, but are not limited to: citric acid, potassium salts of citric acid, and calcium salts of citric acid; phosphoric acid, potassium salts of phosphoric acid, and monobasic calcium salts of phosphoric acid; potassium chlorides; and hydroxy acids which include glycolic, lactic, hydroxybutyric, mandeliec, glycergic, malic, tartaric, and mesotartaric acids, and salts of such hydroxy acids (such salts including potassium and calcium as well as for tartaric acid, dipotassium, dissodium, and diammonium) and potassium bicarbonates. Preferably, the taste-receptor competitors are or include citric acid and potassium salts of phosphoric acid.

The amounts of agents that impart salty and sour taste to be included in the oral liquid composition of the disclosure is any amount which is effective to mask the bitter taste attributable to balsalazide, when combined with effective amounts of artificial sweeteners, and optionally, the flavoring agents. For example, when it is citric acid, the amount of citric acid to be included in the oral composition is preferably from about 0.05% to about 1.2% w/v of the oral composition, more preferably from about 0.10% to about 0.50% w/v, and most preferably about 0.20% w/v of the total weight of the oral composition. When it is dibasic potassium phosphate anhydrous, the amount of di-potassium phosphate to be included in the oral composition is preferably from about 0.25% to about 2.5% of the total weight of the oral composition, more preferably from about 0.50% to about 1.50% w/v, and most preferably about 1.12% w/v of the total weight of the oral composition.

The addition of the dibasic potassium phosphate anhydrous and citric acid also serves the additional function of buffering a balsalazide solution to at least pH 7.0. We have found that an oral solution of balsalazide remains stable at a pH of 7.0 or higher and is unstable under acidic conditions of pH below 7.0. Buffering the balsalazide solution with the dibasic potassium phosphate and citric acid provides a stable oral solution of balsalazide that allow its long-term storage.

Flavors and Preservatives

Flavors incorporated in the composition may be chosen from synthetic flavor oils and flavoring aromatics and/or natural oils, extracts from plant leaves, flowers, fruits, and so forth and combinations thereof. Also useful as flavors are vanilla, citrus oils, including lemon, orange, lime and grape-fruit, and fruit essence, including apple, grape, banana, pear, peach, strawberry, raspberry, cherry, plum, pineapple, apricot, and so forth.

Preservatives, which may be used according to the present disclosure, include, but are not limited to, benzoic acid, sodium benzoate, potassium sorbate, cresol, cetrimide, citric acid and sodium citrate, and alkyl hydroxybenzoates (parabens). Preferably, the preservative is selected from an alkyl hydroxybenzoate, such as methyl hydroxybenzoate, ethyl hydroxybenzoate, propyl hydroxybenzoate (as base or sodium salt) or a combination thereof.

Balsalazide Solutions

Preferably, the liquid compositions are for use in the treatment of children, older people, and many sick patients who often have trouble swallowing tablets or capsules. The liquid suspension may also be used in treatment of animals, as it is convenient and dosage can be accurately controlled.

The carrier/vehicle used in the compositions of the disclosure is preferably water, although other suitable water-containing (aqueous) carriers/vehicles known to the skilled person may also be used. Balsalazide is dissolved or dispersed in an aqueous medium that is transparent and is not cloudy or milky and is bright orange in color. It is presently not known if the aqueous medium containing balsalazide and other ingredients is a true solution or a non-settling dispersion, but it is transparent as would be a true solution or a colloidal dispersion.

The present disclosure of the therapeutic balsalazide chemical composition can be in the form of an aqueous solution, in a dissolvable tablet, or in powder form dispensed in a container such as a sachet. When the tablet or sachet is introduced into an aqueous medium, such as tap water, the tablet or is added to this powder it readily forms a clear solution which can be easily swallowed by the patient.

The effective dosage amounts of balsalazide present in the liquid compositions may vary dependent upon patient needs, but preferably balsalazide is present in the liquid at about 20 to 250 mg/mL (2.5 to 25% w/v) and more preferably at about 75 to 200 mg/mL (7.5 to 20% w/v). Most preferably, the balsalazide is present in the liquid at about 150 mg/m (15% w/v).

Sachets

In one embodiment the sachet may be a hermetically sealed packet made up from any suitable material, such as plastic, metal foil, paper, and combination thereof containing the chemical composition as a loose powder, or granules, or disposed in a tea bag for infusion. The sachet may include a perforated region or a nick in the edge of the sachet for ease of tearing.

The basic sachet formulation comprises: balsalazide or pharmaceutically acceptable salt thereof in the range of from about 52% to about 99% w/w, acesulfame potassium is in the range of from about 0.30% to about 6.0% w/w sucralose is in the range of from 0.30% to about 6.0% w/w, ammonium glycyrrhizinate is in the range of from about 0.10% to about 10.44% w/w. It is understood that the addition of taste receptor competitors, buffering agents, flavorings, and the like will affect these % w/w ranges.

Different product dosage strengths of balsalazide in each sachet can be prepared based on needs of patients to treat and prevent any disease indication for which balsalazide may be prescribed. This can be obtained by filling specific amounts of powder or granulate of this disclosure into unit size sachets. The current prescribed dose of balsalazide is either: one or three 750 mg balsalazide capsules 3 times a day (6.75 g/day); or three 1100 mg balsalazide tablets 2 times a day (6.6 g/day). The powder blend or granular form of the disclosure is placed into multi-dose or unit-dose containers which can provide 750 mg, 2,250 mg and 3,300 mg of balsalazide in unit dose sachets.

An oral liquid solution of balsalazide and single dose sachets will contain the same chemical composition in a pharmaceutically effective concentration. The oral solution may be premixed with an appropriate liquid and made available as a pre-made oral solution. Alternately, the patient or provider will be able to make a solution for administration by adding water to the single dose packet of the same drug product.

An aqueous solution of the chemical composition of the present disclosure in a quantity to provide 750 mg/5 ml of balsalazide disodium may be orally administered for the treatment of mildly to moderately active ulcerative colitis in pediatric and other UC patients. The solution of balsalazide disodium for example, may be administered as follows: Initiate dosage at either 6.75 g/day or 2.25 g/day: A tablespoon i.e. 15 ml of the balsalazide solution (2.25 g balsalazide) is taken by mouth three times a day (i.e., PO TID) for a total daily dose 6.75 g/day. Alternately, 1 teaspoon i.e. 5 ml of the balsalazide solution or (750 mg) PO TID (total dose 2.25 g/day) maybe administered.

A single dose packet of balsalazide disodium for children and other UC patients may be administered as follows: May initiate at either 6.75 g/day or 2.25 g/day, a packet or sachet comprising 2.25 g balsalazide will be emptied into a dosage delivery device and mixed with a tablespoon (15 ml) of water PO TID (total dose 6.75 g/day), or a packet or sachet comprising 750 mg balsalazide will be emptied into a dosage delivery device and mixed with a teaspoon (5 ml) of water PO TID (total dose 2.25 g/day) for administration.

Example 1

A preferred sachet composition for the preparation of a liquid formulation of balsalazide disodium is designated as S-1 in Table 1 below.

TABLE I

Sachet Formulations for Preparing Liquid Formulation of Balsalazide Disodium

| | FORMULATION # | | | | | |
|---|---|---|---|---|---|---|
| | S-1 | | S-2 | | S-3 | |
| COMPONENT: | WEIGHT | % W/W | WEIGHT | % W/W | WEIGHT | % W/W |
| Balsalazide Disodium | 750.0 mg | 85.3 | 750.0 mg | 94.94 | 750.0 mg | 95.2 |
| Sucralose | 10.0 mg | 1.16 | 10.0 mg | 1.26 | 10.0 mg | 1.27 |
| Acesulfame Potassium | 5.0 mg | 0.58 | 5.0 mg | 0.63 | 20.0 mg | 2.54 |
| Amm. Glycyrrhizinate | 25.0 mg | 2.89 | 25.0 mg | 3.16 | 7.5 mg | 0.95 |
| K Dibasic Phosphate | 56.0 mg | 6.48 | 0 | 0 | 0 | 0 |

TABLE I-continued

Sachet Formulations for Preparing Liquid Formulation of Balsalazide Disodium

| | FORMULATION # | | | | | |
|---|---|---|---|---|---|---|
| | S-1 | | S-2 | | S-3 | |
| COMPONENT: | WEIGHT | % W/W | WEIGHT | % W/W | WEIGHT | % W/W |
| Citric Acid | 10.0 mg | 1.16 | 0 | 0 | 0 | 0 |
| Flavorings | 8.5 mg | 0.98 | 0 | 0 | 0 | 0 |
| TOTAL WEIGHT | 864.5 mg | 100 | 790.0 mg | 100 | 787.5 mg | 100 |
| Volume | 5 ml | | 5 ml | | 5 ml | |

In order to reduce the number of inactive ingredients, the formulation S-1 was prepared without the use of citric acid a taste competitor, flavorings and the buffering agent potassium dibasic phosphate. The new composition designated S-2 only contained three sweeteners as inactive ingredients. Volunteers were asked to rate the reduction in bitterness of this formulation and also evaluate an initial taste and an aftertaste as compared to Formulation S-1. The participants found that the formulation S-2 with sweeteners although not optimal was "agreeable". Additional changes in the formulation S-2 were desired to optimize taste and also to make sure that the three sweeteners are present at levels below those in currently marketed drug products and are within the applicable use limits and do not present safety concerns to the patients. FDA use limits for acesulfame potassium and sucralose for oral drug solutions are 10 mg/ml and 40 mg/ml, respectively. FDA use limit for ammonium glycyrrhizinate is 0.1% in total daily diet which is equal to 200 mg.

Sixteen new compositions of balsalazide disodium (750 mg) with different combinations of three sweeteners were prepared. The amounts of acesulfame potassium (10, 20, 30 or 40 mg/sachet) and ammonium glycyrrhizinate (2.5, 5.0, 7.5 or 10 mg/sachet) were varied in new formulations and the concentration of sucralose (10 mg) was kept unchanged.

Participants were asked to rate the reduction in bitterness of these sixteen formulations and also to evaluate an initial taste and an aftertaste as compared to Formulation S-2. The liquid formulation of balsalazide disodium with a combination of sucralose (10 mg), acesulfame potassium (20 mg), and ammonium glycyrrhizinate (7.5 mg) designated S-3 was preferred by the participants. Volunteers found that both initial taste and aftertaste of a balsalazide solution prepared from Sachet S-3 was much more palatable than the balsalazide solution prepared from sachet S-2.

Example 2

A balsalazide capsule contains two excipients colloidal silicon dioxide and magnesium stearate as shown in Table 2 below. These inactive ingredients were included in the S-3 sachet formulation of Table 1 to form the new composition S-4 in Table 2.

TABLE 2

Effect of Excipients on Balsalazide Oral Solution

| | SACHET S-4 FORMULATION | |
|---|---|---|
| COMPONENT | Weight, mg | % W/W |
| Balsalazide Disodium | 750.0 | 94.63 |
| Colloidal Silicon Dioxide | 2.50 | 0.31 |

TABLE 2-continued

Effect of Excipients on Balsalazide Oral Solution

| | SACHET S-4 FORMULATION | |
|---|---|---|
| COMPONENT | Weight, mg | % W/W |
| Magnesium Stearate | 2.50 | 0.31 |
| Acesulfame Potassium | 20.0 | 2.52 |
| Sucralose | 10.0 | 1.26 |
| Ammonium Glycyrrhizinate | 7.5 | 0.95 |
| TOTAL WEIGHT | 792.50 | 100 |

The content of a sachet containing the final formulation S-4, having a 750 mg dose strength, was emptied into a beaker containing the nominally prescribed 5 ml amount of water. The sample was then stirred for 60 seconds at room temperature. A clear homogeneous solution was obtained. These excipients also had no effect on the palatability of the oral solution, volunteers found formulation S-4 as palatable as S-3.

In one embodiment, the sachet formulation comprises: balsalazide or pharmaceutically acceptable salt thereof in the range of from about 52% to about 99% w/w, acesulfame potassium or aspartame is in the range of from about 0.30% to about 6.0% w/w, sucralose is in the range of from 0.30% to about 6.0% w/w, ammonium glycyrrhizinate is in the range of from about 0.10% to about 10.44% w/w, potassium dibasic phosphate anhydrous is in the range of from about 4.10% to about 23.38% w/w, citric acid is in the range of from about 0.73% to about 4.18% w/w, flavor is in the range of from about 0.62% to about 3.55% w/w.

In another embodiment, the sachet formulation comprises: balsalazide or pharmaceutically acceptable salt thereof in the range of from about 77% to about 90% w/w, acesulfame potassium or aspartame is in the range of from about 0.45% to about 1.02% w/w, sucralose is in the range of from 0.90% to about 2.04% w/w, ammonium glycyrrhizinate is in the range of from about 0.10% to about 5.11% w/w, potassium dibasic phosphate anhydrous is in the range of from about 5.02% to about 11.44% w/w, citric acid is in the range of from about 0.90% to about 2.04% w/w, flavor is in the range of from about 0.76% to about 1.74% w/w.

In a further embodiment a sachet formulation comprises: balsalazide or pharmaceutically acceptable salt thereof at about 87% w/w, acesulfame potassium or aspartame at about 0.58% w/w, sucralose is about 1.16% w/w, ammonium glycyrrhizinate is about 2.89% w/w, potassium dibasic phosphate anhydrous is about 6.48% w/w, citric acid is about 1.16% w/w, flavor is about 0.98% w/w.

The dosage form can be effervescent, such as for example, a chewable or rapidly dissolvable effervescent dosage form.

The effervescence can provide a consistent, gentle, steady release of small bubbles, similar to champagne. Effervescence can improve the consumer experience by helping reduce a chalky taste, tooth-packing, and by helping to provide the impression of reduced pressure in the upper gastrointestinal tract. Active ingredients, such as a pH reducing agent and a gas reducer, can also help provide soothing relief of heartburn, acid indigestion, sour stomach and/or gas, while the effervescence provides tactile, visual feedback that the product is working.

Probiotic Supplement

The diagnosis of an inflammatory gastrointestinal disease may likely be accompanied by a prescription for a course of antibiotics. However, such treatment may result in a decrease of intestinal microflora, good and bad, as the antibiotic is likely to reduce the concentration and variety of gastrointestinal microflora. This is undesirable since certain microflora are needed to produce the azoreductase necessary to cleave the diazo bond linking the active agent 5-aminosalicylic acid (5-ASA), to the 4-amino benzoyl-3-alanine ("4-ABA") moiety, thus activating the 5-ASA.

Since azoreductases in intestinal microflora are essential for activation of azo prodrugs in the treatment of inflammatory bowel disease and other gastrointestinal diseases, the kit of our disclosure includes a probiotic to repopulate the colon with non-toxic intestinal microflora necessary for the azoreductase activation of the 5-ASA. Intestinal microflora that have demonstrated non-toxic azoreductase activity include but not limited to beneficial strains of *Bacteroides* sp., beneficial strains of *Butyrivibrio* sp., *Bacillus subtilis*, *Bifidobacterium bifidum*, *Bifidobacterium lactis*, *Bifidobacterium longum*, *Bifobacterium breve*, *Lactobacillus sporogenes*, *Lactobacillus rhamnosus*, *Lactobacillus casei*, *Lactobacillus salivarius*, *Lactobacillus acidophilus*, *Lactobacillus brevis*, *Lactobacillus paracasei*, *Eubacterium* hadrum 1, *Eubacterium* hadrum 2, *Eubacterium* sp., *Clostridium nexile*, *Clostridium* sp., and *Clostridium clostridioforme*.

An empirical approach was used to prepare a palatable liquid formulation of balsalazide. A series of studies were conducted, which led to a palatable liquid balsalazide disodium formulation that provides flexible and convenient dosing and easy to swallow alternative to capsule and tablet dosing for prevention and treatment of G inflammatory diseases. The most salient of these studies are described below.

Example 3: Taste Masking

To determine a palatable liquid formulation of balsalazide, an array of sweeteners and substances that can mask the bitter taste of a balsalazide solution were initially screened with the help of three to five volunteers. These participants were blinded as to the composition of different formulations and were asked to taste 2.5 ml of each sample in random order. The respondents drank water and ate unsalted crackers between samples to remove traces of the first sample tasted. After each taste, participants were asked to rate the reduction in bitterness of the following formulations spanning a time frame from the taste after 10 seconds (an initial taste) to the taste after 10 minutes (an aftertaste) as compared to an oral solution containing 15% (750 mg/5 ml) balsalazide disodium.

Liquid formulation #1 of balsalazide disodium without polyols (sugar alcohols) or added sodium salts was prepared in water as shown in Table 3. No sweeteners were added to Formulation #1 and an initial taste and aftertaste was evaluated by test volunteers. Volunteers unanimously found that balsalazide disodium in aqueous solution has a pungent, bitter and disagreeable medicinal initial taste with somewhat agreeable mild sweet aftertaste.

TABLE 3

Liquid Formulation #1 of Balsalazide Disodium

| Component | Percent W/V |
|---|---|
| Balsalazide disodium | 15 |
| Citric Acid | 0.2 |
| Potassium Dibasic Phosphate Anhydrous | 0.3 |
| Methylparaben | 0.15 |
| Propylparaben | 0.02 |
| Flavorings | 0.17 |
| pH | 4.8 |

Three formulations with different concentrations of natural sweetener sucrose were prepared. All the other excipients of these formulations were the same as in Formulation #1 in TABLE 3. Formulations with Sucrose (20%), Sucrose (40%) and Sucrose (60%) were prepared. Volunteers were asked to rate the reduction in bitterness of these formulations and also evaluate an initial taste and an aftertaste as compared to Formulation #1.

The participants found that these formulations also had a pungent, bitter and medicinal initial taste and mild sweet aftertaste and were not appreciably different than Formulation #1. Moreover, it was observed that the liquid formulations of balsalazide disodium containing 40% sucrose and 60% sucrose were unstable and resulted in precipitation of the drug over time. Additional changes were desired as the bitter taste of balsalazide had not been masked.

Additional liquid formulations of balsalazide disodium comprising an artificial sweetener and the excipients listed in TABLE 4 below were prepared. Each formulation contained a different concentration of a sweetener. Five liquid balsalazide solutions with sucralose (0.10%, 0.60%, 1.0%, 1.5%, or 2.0%); and three each with aspartame (0.50%, 1.0%, or 1.5%), saccharine (0.1%, 0.3%, or 0.5%), acesulfame potassium (0.10%, 0.5%, or 1.0%), and glycyrrhizic acid ammonium (0.1%, 0.5%, or 1.0%) were prepared. Volunteers were asked to rate the reduction in bitterness of these formulations and also evaluate an initial taste and an aftertaste as compared to Formulation #1.

Taste results showed that liquid solutions of balsalazide with saccharine and acesulfame potassium alone were disagreeable and both initial taste and aftertaste was more bitter than Formulation #1. The taste results with liquid solutions of balsalazide containing sucralose, aspartame, or ammonium glycyrrhizinate alone were somewhat encouraging. These artificial sweeteners when added alone at very high concentrations (1% and higher) provided a sweet initial taste but unfortunately this was accompanied by more bitter initial and aftertaste than Formulation #1. Additional changes were desired as the taste had not been optimized.

Ten additional aqueous solutions of balsalazide disodium comprising a combination of two artificial sweeteners and the excipients listed in TABLE 3 were prepared. Each formulation contained two artificial sweeteners (0.50% each) and ten formulations covered all the possible combinations between aspartame, sucralose, saccharine, acesulfame potassium, and ammonium glycyrrhizinate. Volunteers were asked to rate the reduction in bitterness of these formulations and also evaluate an initial taste and an aftertaste as compared to Formulation #1.

The participants concluded that the taste of ten liquid formulations of balsalazide each with a different combination of two sweeteners was unacceptable. Both initial taste and aftertaste of balsalazide was more bitter than Formulation #1.

Now that a combination of two sweeteners did not give desired results, a combination of three sweeteners, was used to prepare another set of ten formulations again keeping all other excipients the same as listed in TABLE 3. Each formulation contained three artificial sweeteners (0.30% each) that covered all the possible combinations between aspartame, sucralose, saccharine, acesulfame potassium, and ammonium glycyrrhizinate. Participants were asked to rate the reduction in bitterness of these formulations and also evaluate an initial taste and an aftertaste as compared to Formulation #1.

The liquid formulation of balsalazide with a combination of sucralose, aspartame, and ammonium glycyrrhizinate was preferred by the participants. Volunteers found that both initial taste and aftertaste of a balsalazide solution with a combination of sucralose, aspartame, and ammonium glycyrrhizinate was much more tolerable than the balsalazide solution of Formulation #1, the liquid formulation of balsalazide used as an unacceptable reference for comparison.

The amounts of each sweetener in a liquid composition of balsalazide with a combination of sucralose, aspartame, and ammonium glycyrrhizinate were further optimized for initial and aftertaste by preparing and taste evaluations of additional formulations. An exemplary formulation is shown in TABLE 4.

TABLE 4

Preferred Liquid Formulation #2 of Balsalazide Disodium

| Component | LIQUID SOLUTION Percent W/V; g/mL |
|---|---|
| Balsalazide disodium | 15.00 |
| Aspartame | 0.10 |
| Sucralose | 0.20 |
| Ammonium Glycyrrhizinate | 0.50 |
| Potassium Dibasic Phosphate Anhydrous | 0.30 |
| Citric Acid | 0.20 |
| Methylparaben | 0.15 |
| Propylparaben | 0.02 |
| Flavorings | 0.17 |
| PH | 4.80 |
| TOTAL | 100 mL |

The artificial sweetener composition of the present disclosure is also surprising in that it provides a stable oral solution of balsalazide that allow its long-term storage only at neutral pH of 7.0 and above and is unstable under acidic conditions of pH below 7.0. Increasing the taste competitor potassium dibasic phosphate anhydrous took advantage of its pH buffering characteristic to control the pH of the balsalazide formulation to above pH 7.0. Another formulation with a final pH of 7.2 was prepared after it was confirmed that balsalazide is unstable at pH below 7.0 and this was confirmed by testing the degradation of balsalazide following 3-months storage at room temperature and 40 C. As the sweetener aspartame is unstable in solution at pH 7.0 and above it was replaced with the sweetener acesulfame potassium. After another round of taste testing the liquid formulation #3 shown in TABLE 5 became the most acceptable formulation in terms of taste tolerability and stability. Lemon and Tutti Fruitti were the top two flavors of choice amongst many tested by the participants.

TABLE 5

Preferred Liquid Formulation #3 of Balsalazide Disodium

| Component | LIQUID SOLUTION Percent W/V; g/mL |
|---|---|
| Balsalazide disodium | 15.00 |
| Acesulfame Potassium | 0.10 |
| Sucralose | 0.20 |
| Ammonium Glycyrrhizinate | 0.50 |
| Potassium Dibasic Phosphate Anhydrous | 1.12 |
| Citric Acid | 0.20 |
| Methylparaben | 0.15 |
| Propylparaben | 0.02 |
| Flavorings | 0.17 |
| pH | 7.2 |
| TOTAL | 100 mL |

Example: Storage Stability of Liquid Balsalazide Solution

Balsalazide disodium may degrade under the influence of light, the process was performed shielded from direct sunlight. The basic steps are as follows.

After weighing the excipients and the active ingredient, a balsalazide disodium solution was prepared comprising components shown in TABLE 5 in the following manner. In a water bath, 50 ml of water was heated to 70° C. and 0.15 g methylparaben and 0.02 g propylparaben were added to the heated water. The solution was stirred with an overhead polytron stirrer at about 300 rpm. After the parabens were completely dissolved, a clear solution was cooled to room temperature and following components were added with stirring 0.20 g of anhydrous citric acid, 1.12 g potassium dibasic phosphate anhydrous, 0.50 g ammonium glycyrrhizinate, 0.20 g sucralose, and 0.10 g acesulfame potassium. After all the ingredients were dissolved, 15 g of balsalazide disodium was slowly added into the mixture with stirring. The final mixture was stirred at room temperature until a clear homogeneous solution was obtained. After that, the pH of the solution was adjusted to approximately 7.2 by adding either citric acid or potassium dibasic potassium and the volume was adjusted to 100 ml by adding water. The final solution was filtered with a suitable filter, and filled in light-protective containers, such as amber type glass 100 ml bottles sealed with child resistant, tamper-evident screw caps.

The storage stability of two balsalazide disodium solutions, 750 mg/5 ml, with the formulations described in TABLE 6 and TABLE 7 with pH of 4.8 and pH 7.2, respectively were subjected to accelerated stability testing at 40° C. and at room temperature (25° C.). Balsalazide solutions stored in amber PVC bottles (30 ml volume) were tested over a 90-day storage period. The amount of balsalazide and its known impurities were determined by a validated high pressure liquid chromatography (HPLC) assay after 0 day (initial), 45 days, and 90 days and results are shown in TABLE 6 below. Five minor impurities (less than 0.1% each) were identified in balsalazide solution initially on day 0. These impurities increased substantially in balsalazide solution with storage time and temperature in pH 4.8 solution, both at 25° C. and 40° C. There was an appreciable settling of drug in pH 4.8 balsalazide solution with time at 25° C. after storage of 45 days and the settling of the drug continued to increase substantially by 90 days (TABLE 6). The settling of balsalazide is also reflected by significantly lower recovery of the drug in pH 4.8 solution after 90-day storage at both the temperatures.

TABLE 6

Storage Stability of Balsalazide Solution pH 4.8

| COMPONENT | Balsalazide Solution 750 mg/5 mL; pH 4.8 | | | | |
|---|---|---|---|---|---|
| Storage Time, | | 45 Days | | 90 Days | |
| Temp | Initial | 25° C. | 40° C. | 25° C. | 40° C. |
| Balsalazide, % | 100 ± 4 | 99 ± 6 | 99 ± 5 | 87 ± 5 | 91 ± 4 |
| Impurity 1, % | 0.045 | 0.087 | 0.067 | 0.158 | 0.303 |
| Impurity 2, % | 0.034 | 0.021 | 0.021 | 0.068 | 0.082 |
| Impurity 3, % | 0.004 | 0.019 | 0.045 | 0.057 | 0.104 |
| Impurity 4, % | 0.007 | 0.041 | 0.042 | 0.012 | 0.013 |
| Impurity 5, % | 0.006 | 0.018 | 0.019 | 0.019 | 0.020 |
| Physical Stability (Settling of Drug) | NONE | SIGNIFICANT SETTLING at 25° C. | | SIGNIFICANT SETTLING at 25° C. | |

In contrast, there was no significant increase of impurities in balsalazide solution with time in pH 7.2 formulation, at 25° C. and 40° C. (TABLE 7). No settling of drug was observed in balsalazide solution with time at pH 7.2, both at 251° C. and 40° C. (TABLE 7). The solution at pH 7.2 was clear after 90-days of storage both at 25° C. and 40° C. Almost all of the drug was recovered in pH7.2 solution after 90-day storage.

TABLE 7

Storage Stability of Balsalazide Solution pH 7.2

| COMPONENT | Balsalazide Solution 750 mg/5 mL; pH 4.8 | | | | |
|---|---|---|---|---|---|
| Storage Time, | | 45 Days | | 90 Days | |
| Temp | Initial | 25° C. | 40° C. | 25° C. | 40° C. |
| Balsalazide, % | 101 ± 3 | 105 ± 3 | 103 ± 3 | 101 ± 2 | 102 ± 3 |
| Impurity 1, % | 0.035 | 0.053 | 0.032 | 0.030 | 0.032 |
| Impurity 2, % | 0.019 | 0.015 | 0.010 | 0.012 | 0.015 |
| Impurity 3, % | 0.017 | 0.023 | 0.015 | 0.020 | 0.031 |
| Impurity 4, % | 0.061 | 0.058 | 0.073 | 0.054 | 0.045 |
| Impurity 5, % | 0.021 | 0.013 | 0.003 | 0.010 | 0.021 |
| Physical Stability (Settling of Drug) | NONE | NONE | | NONE | |

TABLE 8

Sachet Formulation for Preparing Liquid Formulation of Different Dose Strength

| COMPONENT | Balsalazide Dose Strengths | | Percent W/W |
|---|---|---|---|
| Balsalazide Disodium | 750.0 mg | 2,250.0 mg | 86.75 |
| Acesulfame Potassium | 5.0 mg | 15.0 mg | 0.58 |
| Sucralose | 10.0 mg | 30.0 mg | 1.16 |
| Ammonium Glycyrrhizinate | 25.0 mg | 75.0 mg | 2.89 |
| Potassium Dibasic Phosphate | 56.0 mg | 168.0 mg | 6.48 |
| Citric Acid | 10.0 mg | 30.0 mg | 1.16 |
| Flavorings | 8.5 mg | 25.5 mg | 0.98 |
| TOTAL WEIGHT | 864.5 mg | 2,593.5 mg | 100 |
| VOLUME | 5 mL | 15 L | |

1) Above formulation (TABLE 8) is prepared by a method comprising the following:
  1. Balsalazide disodium, sucralose, acesulfame potassium, ammonium glycyrrhizinate, potassium dibasic phosphate anhydrous, citric acid, and flavorings are mixed in a container.
  2. The powder mixture is sieved by using a suitable screen and transferred into a container and mixed.
  3. Total powder corresponding to different single dose strengths of balsalazide disodium including 750 mg, 2,250 mg and 3,300 mg are packed in sealed vessels such as sachets.
  4. Optionally, the sealed sachets may be dispensed either individually, as many as is needed for a prescribed course of treatment. Moreover, the dosage of balsalazide in each sachet may be adjusted to accommodate smaller or larger dosages in accordance with a prescribed therapy.

The content of a sachet containing the final formulation, having a 750 mg dose strength and prepared as described in TABLE 8, was emptied into a beaker containing the nominally prescribed 5 ml amount of water. The sample was then stirred for 60 seconds at room temperature. A clear homogeneous solution was obtained.

In another embodiment rapid dissolution may be obtained by mixing a chemical composition in the range of 52% w/w to 92% w/w with anhydrous citric acid in the range of 1% w/w to 10% w/w and potassium bicarbonate in the range of 1% w/w to 10% w/w, to provide a composition for rapid effervescent aqueous dissolution, and optionally tableting the effervescent composition to provide a therapeutically sufficient unit dose of the chemical composition as an effervescent rapidly dissolving tablet when introduced to a liquid.

Referring now to the figures, FIG. 1 shows an example of a blister pack with therapeutic dose and probiotic 130 in accordance with aspects of the present disclosure. The example shown includes first layer 100, second layer 105, perforation 110, chemical composition 115, and probiotic 130.

In some examples, the chemical composition 115 is mixed in the range of 52% w/w to 99% w/w with anhydrous citric acid in the range of 0.9% w/w to 10% w/w and potassium bicarbonate in the range of 1% w/w to 10% w/w, to provide an effervescent composition for rapid aqueous dissolution. In some examples, the effervescent composition is formed into tablets to provide a therapeutically sufficient unit dose of the chemical composition when dissolved in a liquid. In some examples, the chemical composition 115 is packaged with a probiotic 130 in accordance with a prescribed course of treatment.

Chemical composition 115 may be an example of, or include aspects of, the corresponding element described with reference to FIGS. 2, 3, and 4. Chemical composition 115 may include prodrug 120 and sweetener composition 125.

The prodrug 120 may be selected from at least one of balsalazide, balsalazide disodium, sulfasalazine, olsalazine and ipsalazine, the positional balsalazide isomer 4-aminosalicylic acid, linked to 4-amino benzoyl-3-alanine and its disodium salt in the range from about 52% w/w to 99% w/w of the chemical composition, the therapeutic dose being sufficient to provide between 750 mg to 3,300 mg of the therapeutic agent.

The sweetener 125 may be composition for mitigating the bitterness of the therapeutic agent comprising sucralose in the range of 0.3% w/w to 6.0% w/w of the chemical composition, acesulfame potassium in the range of 0.3% w/w to 6.0% w/w of the chemical composition, ammonium glycyrrhizinate in the range of 0.10% w/w to 10.44% w/w of the chemical composition, and less than 0.01% of a polyol. In some examples, the prodrug 120 is balsalazide disodium and the sweetener 125 composition is polyol-free.

Probiotic 130 may be an example of, or include aspects of, the corresponding element described with reference to FIGS. 3 and 4.

Figure 2:
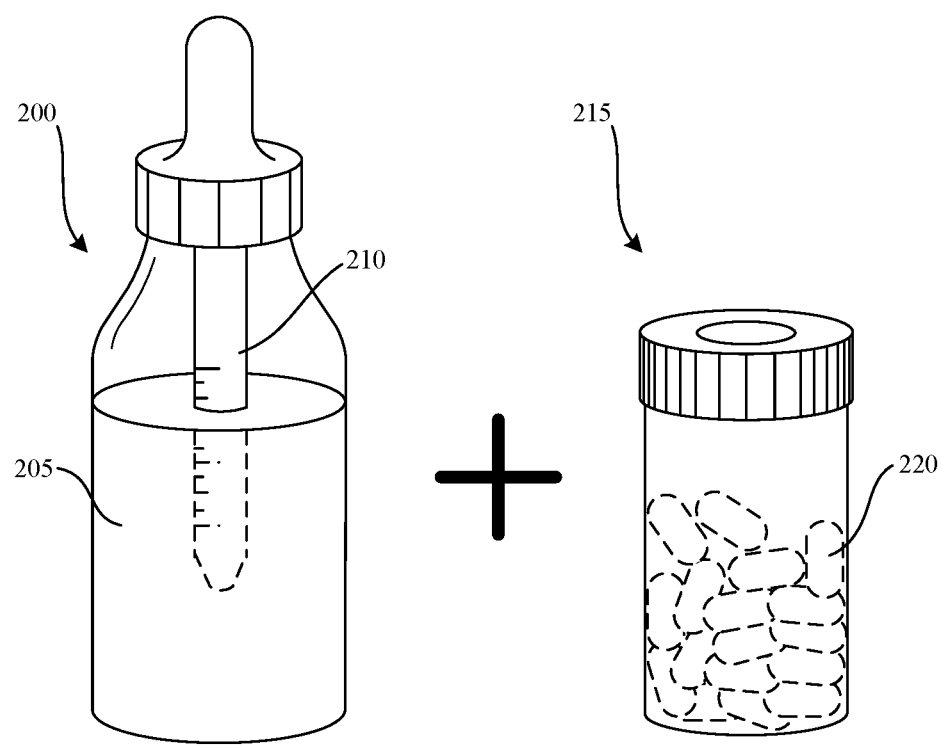
FIG. 2 shows an example of an aqueous balsalazide solution with dropper and probiotic pills in accordance with aspects of the present disclosure.

FIG. 2 shows an example of an aqueous balsalazide with dropper 210 and probiotic pills 220 in accordance with aspects of the present disclosure. The example shown includes liquid container 200 and pill container 215. Liquid container 200 may include chemical composition 205 and dropper 210. Pill container 215 may include probiotic pill 220.

In some examples, the chemical composition 205 is mixed in the range of 52% w/w to 99% w/w with anhydrous citric acid in the range of 0.9% w/w to 10% w/w and potassium bicarbonate in the range of 1% w/w to 10% w/w, to provide an effervescent composition for rapid aqueous dissolution. In some examples, the effervescent composition is formed into tablets to provide a therapeutically sufficient unit dose of the chemical composition when dissolved in a liquid. In some examples, the chemical composition 205 is packaged with a probiotic are in accordance with a prescribed course of treatment. Chemical composition 205 may be an example of, or include aspects of, the corresponding element described with reference to FIGS. 1, 3, and 4.

Figure 3:
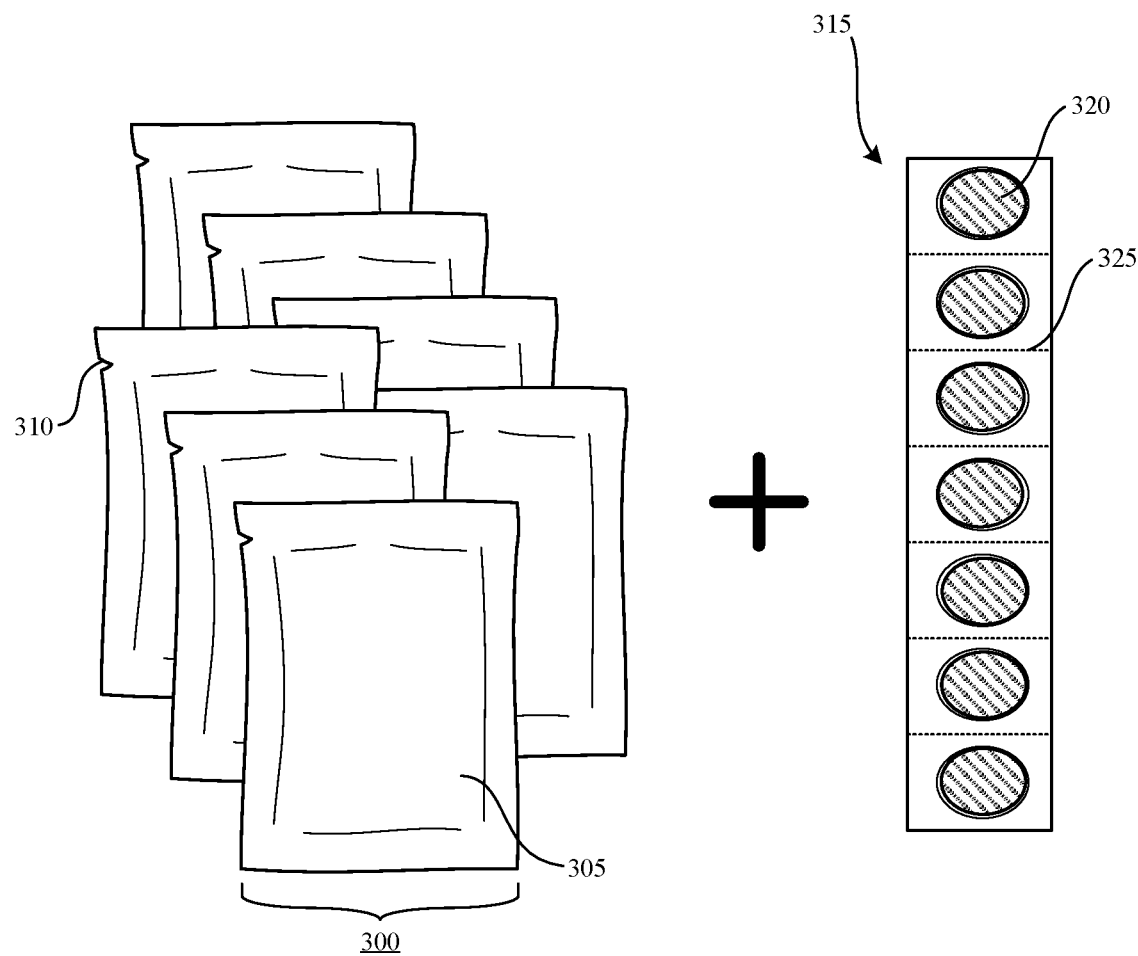
FIG. 3 shows an example of a sachet with a therapeutic dose and a blister pack with probiotic pills in accordance with aspects of the present disclosure.

FIG. 3 shows an example of a sachet 300 with a therapeutic dose and a blister pack 315 with probiotic 320 pills in accordance with aspects of the present disclosure. The example shown includes sachet 300 and blister pack 315. Blister pack 315 may include probiotic 320 and perforation 325.

In some examples, the chemical composition 305 is packaged as a therapeutically sufficient dose into a sachet 300. In some examples, the sachet 300 is packaged as a plurality of sachets 300 into a container to provide a quantity of sachets 300 sufficient for a course of treatment. Sachet 300 may be an example of, or include aspects of, the corresponding element described with reference to FIG. 4. Sachet 300 may include chemical composition 305 and tear 310.

In some examples, the chemical composition 305 is mixed in the range of 52% w/w to 99% w/w with anhydrous citric acid in the range of 1% w/w to 10% w/w and potassium bicarbonate in the range of 1% w/w to 10% w/w, to provide an effervescent composition for rapid aqueous dissolution. In some examples, the effervescent composition is formed into tablets to provide a therapeutically sufficient unit dose of the chemical composition when dissolved in a liquid. In some examples, the chemical composition 305 is packaged with a probiotic 320 are in accordance with a prescribed course of treatment.

Chemical composition 305 may be an example of, or include aspects of, the corresponding element described with reference to FIGS. 1, 2, and 4. Probiotic 320 may be an example of, or include aspects of, the corresponding element described with reference to FIGS. 1 and 4.

Figure 4:
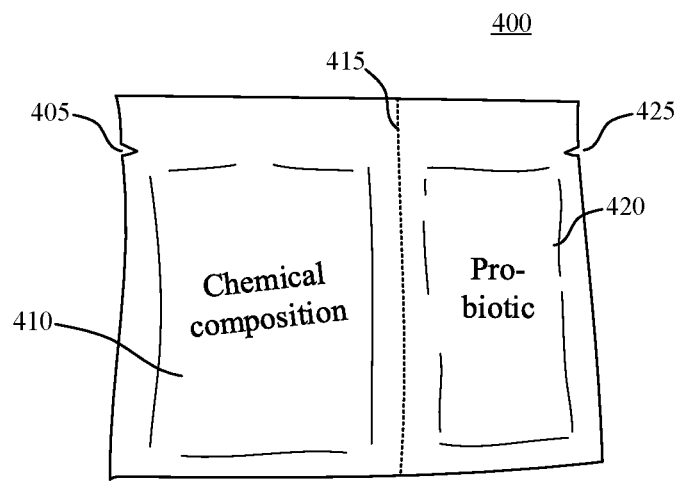
FIG. 4 shows an example of a sachet containing both a therapeutic dose and a probiotic in accordance with aspects of the present disclosure.

FIG. 4 shows an example of a sachet 400 containing both a therapeutic dose and a probiotic 420 in accordance with aspects of the present disclosure. The example shown includes sachet 400. In some examples, the chemical composition 410 is packaged in a therapeutically sufficient dose into a sachet 400. In some examples, the sachet 400 is packaged with a plurality of sachets 400 into a container to provide a quantity of sachets 400 sufficient for a course of treatment.

Sachet 400 may be an example of, or include aspects of, the corresponding element described with reference to FIG. 3. Sachet 400 may include therapeutic dose tear 405, chemical composition 410, perforation 415, probiotic 420, and probiotic tear 425.

In some examples, the chemical composition 410 is mixed in the range of 52% w/w to 92% w/w with anhydrous citric acid in the range of 1% w/w to 10% w/w and potassium bicarbonate in the range of 1% w/w to 10% w/w, to provide an effervescent composition for rapid aqueous dissolution. In some examples, the effervescent composition is formed into tablets to provide a therapeutically sufficient unit dose of the chemical composition when dissolved in a liquid. In some examples, the chemical composition 410 is packaged with a probiotic 420 are in accordance with a prescribed course of treatment.

Chemical composition 410 may be an example of, or include aspects of, the corresponding element described with reference to FIGS. 1, 2, and 3. Probiotic 420 may be an example of, or include aspects of, the corresponding element described with reference to FIGS. 1 and 3.

Figure 5:
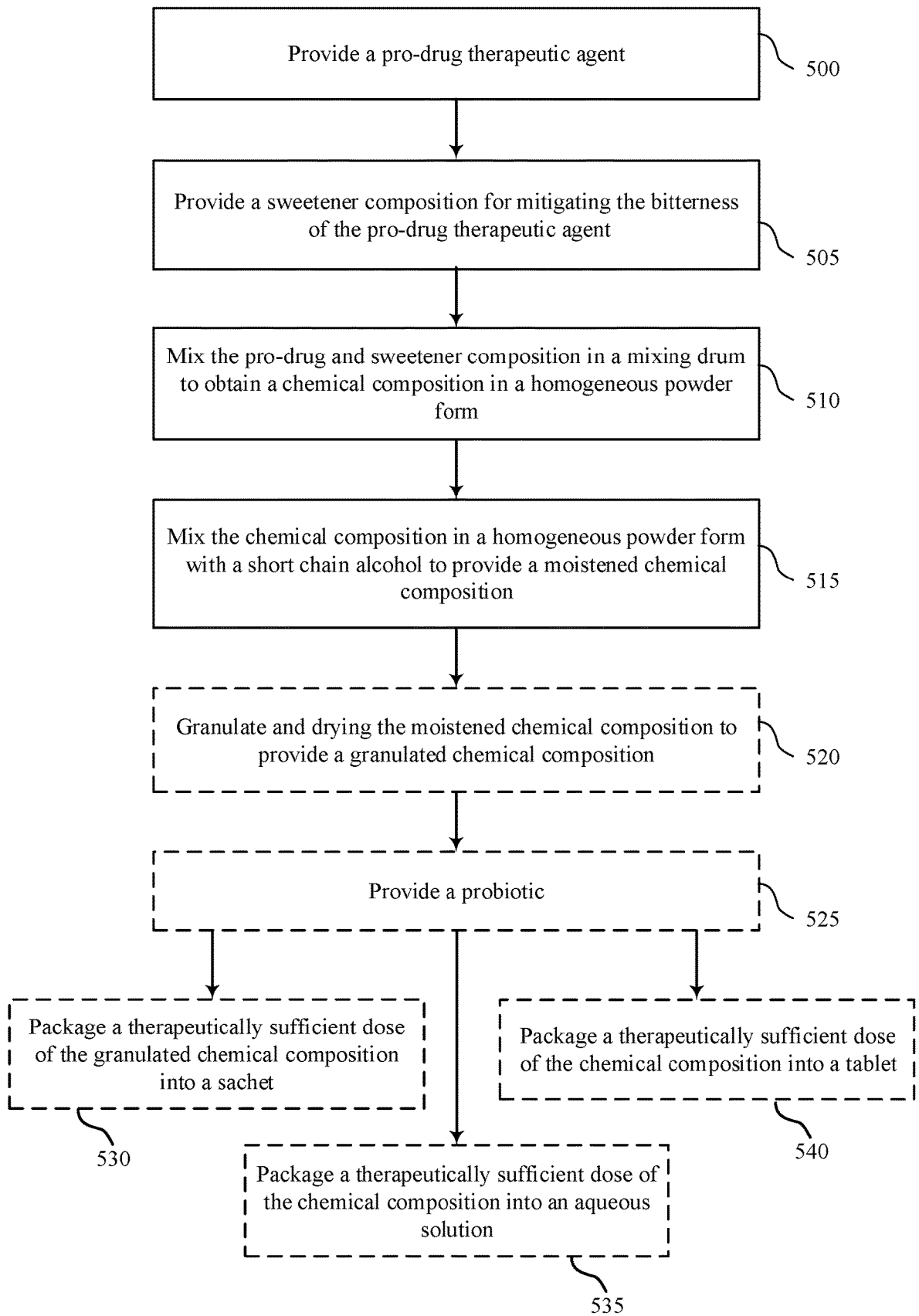
FIG. 5 shows an example of preparing a therapeutic dose of a chemical composition in accordance with aspects of the present disclosure.

FIG. 5 shows an example of preparing a therapeutic dose of a chemical composition in accordance with aspects of the present disclosure. In some examples, one or more of these operations may be performed manually, or with the assistance of one or more tools. In some examples, one or more of these operations may be performed by a machine including a processor executing a set of codes to control functional elements of an apparatus. Additionally, or alternatively, the processes may be performed using special-purpose hardware. Generally, these operations may be performed according to the methods and processes described in accordance with aspects of the present disclosure. For example, the operations may be composed of various substeps, or may be performed in conjunction with other operations described herein.

At step 500, a system for preparing the therapeutic dose of a chemical composition may include providing a prodrug therapeutic agent, the prodrug selected from at least one of balsalazide, balsalazide disodium, sulfasalazine, olsalazine and ipsalazine, the positional balsalazide isomer 4-aminosalicylic acid, linked to 4-amino benzoyl-3-alanine and its disodium salt in the range from about 52% w/w to 99% w/w of the chemical composition, the therapeutic dose being sufficient to provide between 750 mg to 3,300 mg of the therapeutic agent. In some cases, the product of this step may be a prodrug as described with reference to FIG. 1.

At step 505, a system for preparing the therapeutic dose of a chemical composition may include providing a sweetener composition for mitigating the bitterness of the therapeutic agent comprising sucralose in the range of 0.3% w/w to 6.0% w/w of the chemical composition, acesulfame potassium in the range of 0.3% w/w to 6.0% w/w of the chemical composition, ammonium glycyrrhizinate in the range of 0.1% w/w to 10.34% w/w of the chemical composition, and less than 0.01% of a polyol. In some cases, the product of this step may be a sweetener as described with reference to FIG. 1.

At step 510, a system for preparing the therapeutic dose of a chemical composition may include mixing the chemical composition in a mixing drum to obtain the chemical composition in a homogeneous powder form.

At step 515, a system for preparing the therapeutic dose of a chemical composition may include mixing the chemical composition in a homogeneous powder form with a short chain alcohol to provide a moistened chemical composition.

At step 520, in some embodiments, a system for preparing the therapeutic dose of a chemical composition may include granulating and drying the moistened chemical composition to provide a granulated chemical composition.

At step 525, in some embodiments, a system for preparing the therapeutic dose of a chemical composition may include providing a probiotic.

At step 530, in some embodiments, a system for preparing the therapeutic dose of a chemical composition may include packaging a therapeutically sufficient dose of the granulated chemical composition into a sachet.

At step 535, in some embodiments, a system for preparing the therapeutic dose of a chemical composition may include dissolving a therapeutically sufficient dose of the chemical composition into an aqueous solution.

At step 540, in some embodiments, a system for preparing the therapeutic dose of a chemical composition may include tableting a therapeutically sufficient dose of the chemical composition into a tablet.

Those skilled in the art to which the present disclosure pertains may make modifications resulting in other embodiments employing principles of the present disclosure without departing from its spirit or characteristics, particularly upon considering the foregoing teachings. Accordingly, the described embodiments are to be considered in all respects only as illustrative, and not restrictive, and the scope of the present disclosure is, therefore, indicated by the appended claims rather than by the foregoing description or drawings. Consequently, while the present disclosure has been described with reference to particular embodiments, modifications of structure, sequence, materials and the like apparent to those skilled in the art still fall within the scope of the disclosure as claimed by the Applicant.

The description and drawings described herein represent example configurations and do not represent all the implementations within the scope of the claims. For example, the operations and steps may be rearranged, combined or otherwise modified. Also, structures and devices may be represented in the form of block diagrams to represent the relationship between components and avoid obscuring the described concepts. Similar components or features may have the same name but may have different reference numbers corresponding to different figures.

Some modifications to the disclosure may be readily apparent to those skilled in the art, and the principles defined herein may be applied to other variations without departing from the scope of the disclosure. Thus, the disclosure is not limited to the examples and designs described herein, but is to be accorded the broadest scope consistent with the principles and novel features disclosed herein.

In this disclosure and the following claims, the word "or" indicates an inclusive list such that, for example, the list of X, Y, or Z means X or Y or Z or XY or XZ or YZ or XYZ. Also the phrase "based on" is not used to represent a closed set of conditions. For example, a step that is described as "based on condition A" may be based on both condition A and condition B. In other words, the phrase "based on" shall be construed to mean "based at least in part on."

What is claimed is:

1. A therapeutic composition for treatment of a gastrointestinal disease in a subject in need thereof, comprising:
   a therapeutically effective amount of a diazo pro-drug, and
   a combination of sweeteners comprising sucralose, ammonium glycyrrhizinate, and at least one of aspartame and acesulfame potassium;
   wherein the composition is essentially free of sugar alcohols; and
   wherein the therapeutic composition is embodied in a liquid formulation, comprising:
   15.00% w/v balsalazide disodium,
   0.10% w/v acesulfame potassium,
   0.20% w/v sucralose,
   0.50% w/v ammonium glycyrrhizinate,
   1.12% w/v potassium dibasic phosphate anhydrous,
   0.20% w/v citric acid,
   0.15% w/v methylparaben, and
   0.02% w/v propylparaben.

* * * * *